US005661406A

United States Patent [19]

Daily et al.

[11] Patent Number: 5,661,406

[45] Date of Patent: Aug. 26, 1997

[54] METHODS FOR DETECTING AND LOCATING LEAKS IN CONTAINMENT FACILITIES USING ELECTRICAL POTENTIAL DATA AND ELECTRICAL RESISTANCE TOMOGRAPHIC IMAGING TECHNIQUES

[75] Inventors: William D. Daily, Livermore, Calif.; Daren L. Laine, San Antonio, Tex.; Edwin F. Laine, Alamo, Calif.

[73] Assignee: Leak Location Services, Inc., San Antonio, Tex.

[21] Appl. No.: 534,620

[22] Filed: Sep. 27, 1995

[51] Int. Cl.$^6$ .......................... G01R 27/08; G01N 27/00; G08B 21/00

[52] U.S. Cl. .......................... 324/713; 324/557; 340/605

[58] Field of Search .......................... 324/557, 713, 324/715, 718, 559, 546; 340/605

[56] References Cited

U.S. PATENT DOCUMENTS

| | | | |
|---|---|---|---|
| 3,383,863 | 5/1968 | Berry | 324/557 |
| 4,719,407 | 1/1988 | Converse et al. | 324/546 |
| 4,720,669 | 1/1988 | Owen | 324/546 |
| 4,725,785 | 2/1988 | Converse et al. | 324/559 |
| 4,740,757 | 4/1988 | Converse et al. | 324/559 |
| 4,751,467 | 6/1988 | Cooper | 324/557 |
| 4,751,841 | 6/1988 | Biard et al. | 73/49 |
| 4,755,757 | 7/1988 | Cooper | 324/557 |
| 4,905,210 | 2/1990 | Owen | 367/128 |
| 4,947,470 | 8/1990 | Darilek | 324/557 |
| 4,950,374 | 8/1990 | Darilek et al. | 204/180 |
| 5,357,202 | 10/1994 | Henderson | 324/357 |
| 5,460,032 | 10/1995 | Hampton | 324/557 |

FOREIGN PATENT DOCUMENTS

WO9/02822 3/1994 WIPO .

OTHER PUBLICATIONS

Steve Barrie and Vladimir Hruby Aug. 1994 "Testing the integrity of landfill liners through monitoring", *Wastes Management*, p. 34.

Thomas J. Yorkey et al., Nov. 1987 "Comparing Reconstruction Algorithms for Electrical Impedance Tomography", *IEEE Transactions on Biomedical Engineering*, vol. BME 34, No. 11, pp. 843–852.

*Primary Examiner*—Vinh P. Nguyen
*Assistant Examiner*—Thomas Valone
*Attorney, Agent, or Firm*—Gunn, Lee & Miller, P.C.

[57] ABSTRACT

Methods are provided for detecting and locating leaks in liners used as barriers in the construction of landfills, surface impoundments, water reservoirs, tanks, and the like. Electrodes are placed in the ground around the periphery of the facility, in the leak detection zone located between two liners if present, and/or within the containment facility. Electrical resistivity data is collected using these electrodes. This data is used to map the electrical resistivity distribution beneath the containment liner between two liners in a double-lined facility. In an alternative embodiment, an electrode placed within the lined facility is driven to an electrical potential with respect to another electrode placed at a distance from the lined facility (mise-a-la-masse). Voltage differences are then measured between various combinations of additional electrodes placed in the soil on the periphery of the facility, the leak detection zone, or within the facility. A leak of liquid though the liner material will result in an electrical potential distribution that can be measured at the electrodes. The leak position is located by determining the coordinates of an electrical current source pole that best fits the measured potentials with the constraints of the known or assumed resistivity distribution.

3 Claims, 3 Drawing Sheets

METHODS FOR DETECTING AND LOCATING LEAKS IN CONTAINMENT FACILITIES USING ELECTRICAL POTENTIAL DATA AND ELECTRICAL RESISTANCE TOMOGRAPHIC IMAGING TECHNIQUES

RIGHTS STATEMENT

The United States government has rights in this invention pursuant to contract W-7405-ENG-48 between the United States Department of Energy and the University of California for the operation of the Lawrence Livermore National Laboratory.

BACKGROUND OF THE INVENTION

1. Field of the Invention

This invention relates generally to methods for the detection and location of leaks in containment facilities such as landfills, surface impoundments, storage tanks, or other like structures. This invention relates more specifically to methods for the detection and location of leaks in geomembrane lined containment facilities and the like, using mise-á-la-masse methods for collecting electrical potential data, mathematical inversion methods for characterizing electrical resistivity, and electrical resistivity tomography (ERT) methods. The methods are applicable to detecting and locating leaks in both newly installed and existing geomembrane lined containments and the like.

2. Description of the Related Art

The primary purpose of geomembrane liners, steel liners, and concrete liners utilized in various types of storage facilities is to provide barriers for liquids contained within the facility in order to prevent the leakage of these liquids into the surrounding environment. The detection and location of leaks in such liners is therefore a critical element in preventing environmental problems such as groundwater pollution and the like. Typical examples of such lined facilities include water reservoirs, surface impoundments, steel tanks, concrete tanks, landfills, leach pads, and other types of liquid and semi-liquid containment facilities. The majority of these facilities, especially those that contain groundwater contaminants, are lined with geomembrane liners.

During geomembrane liner installation the liner is box methods, air lance methods, spark testing methods, air pressure testing methods, or other types of well known test methods. These conventional test methods are typically limited to the testing of the liner seam areas. The majority of the liner is, therefore, only visually inspected for leaks.

More recently, electrical leak location methods have been used to detect and locate leaks in geomembrane liners. These electrical methods are capable of testing 100% of the liner area that is covered with water or soil. All of these existing test methods, however, including the electrical methods, require access to the interior of the containment facility by field personnel, or the placement of an electrical wire grid system under or on top of the geomembrane during construction. Electrical leak location methods are the only field proven methods that can locate leaks in a geomembrane liner when soil is placed over the liner. However, even the existing electrical methods require the collection of an array of electrical potential data on the surface of the soil using a close spaced survey grid of some type. A test method is therefore needed that can remotely and automatically detect and locate leaks in both new and existing liners without the need for an extensive survey grid.

U.S. Pat. Nos. 4,543,525; 4,719,407; 4,725,785; 4,720,669; 7,751,841; 4,751,467; 4,755,757; and 4,740,757, are all directed to various systems and methods for electrically detecting and locating leaks in geomembrane liners. All of these systems, however, require either the extensive sensor grid structure described above, or require direct access by test operators to the interior liquid or sludge contained in the impoundment. Many of the systems described in these earlier patents involve complex and extensive electrical structures that must often be installed during the installation of the liner.

SUMMARY OF THE INVENTION

It is therefore an object of this invention to eliminate the necessity of accessing the interior of a lined containment facility in order to test the containment liner for leaks. This is accomplished by making electrical measurements around the periphery of the liner, under the liner, or within the facility, and using computer software to process the electrical potential and/or electrical resistivity survey data.

Another object of this invention is to eliminate the need for collecting large amounts of electrical potential data in a close spaced grid pattern and to allow reduced amounts of data to be collected using widely spaced monopoles, dipoles, linear dipoles, broadside dipoles, or other electrode configurations.

Another object of this invention is to enable a containment facility to be monitored for leaks from a remote location and on a periodic basis, to warn facility operators of potential problems.

Another object of this invention is to detect and locate leaks at sites that contain material that can not be removed, by making measurements around the periphery, on top of the existing material, or between two liners within the facility.

Another object of this invention is to detect leaks in steel or concrete storage tanks by methods similar to those utilized in geomembrane lined facilities so as to eliminate the need for access to the interior of such containment vessels.

The methods of the present invention utilize electrical potential and electrical resistance measurements within the contents of the containment facility and within the sub-surface outside the facility, to detect and locate the presence of leaks in the lined containment. In most cases, it is assumed that the contents of the facility are electrically isolated from the sub-surface outside the facility by a geomembrane type liner which acts as a barrier to electric current flow. The methods of the present invention are, however, applicable to a containment facility constructed with an electrically conductive shell or barrier.

In a first method of the present invention, the contents of the containment facility are excited to an electrical potential above the surrounding soil. Any location where an electrically conductive liquid can pass through the liner and enter the sub-soil will also pass an electric current. The presence of this current demonstrates a fluid leak in the liner. In the first method, the electrical potential distribution set up in the sub-surface soil and within the contents of the facility due to the current flow through the liner is sensed by measuring the electrical potential at a series of electrodes (either outside the facility, in the soil, or inside the facility) and determining from the electrical potential profile, the location of the electric current flowing through the liner.

In a second method of the present invention, the electrical measurements detect and characterize changes in the electrical resistivity within the sub-surface soil outside of the containment facility. A base-line resistivity image is constructed and is later compared with subsequent resistivity images to detect and locate leak points in the liner. The electrical resistivity profile identifies changes in the subsurface electrical characteristics brought about by the flow of a conductive liquid through the liner.

Other objects and applications of the methods of the present invention will become apparent from a reading of the following detailed description and the appended claims.

DESCRIPTION OF THE PREFERRED EMBODIMENT

The present invention uses a relatively simple hardware system of electrical probes in conjunction with appropriate voltage, current, and resistivity measuring devices to apply mise-á-la-masse electrical potential and resistivity measurement techniques to detect leaks in geomembrane lined, steel lined, concrete lined, or similar type facilities. The methods of the present invention further use mathematical inversion calculations to determine the location of the path of an electrical current passing through the liner of a containment facility, which path is indicative of the location of the leak, as long as the liquid being contained is electrically conducting. In addition, Electrical Resistivity Tomography (ERT) imaging methods are used to calculate the resistivity distribution under the containment facility. This calculated distribution can be used in two ways: (1) for the mise-á-la-masse technique to calculate current paths beneath the facility and thus determine the source point(s) (leaks); (2) for the ERT technique to calculate resistivity distribution beneath the facility and thus changes indicative of a leak.

Figure 1:
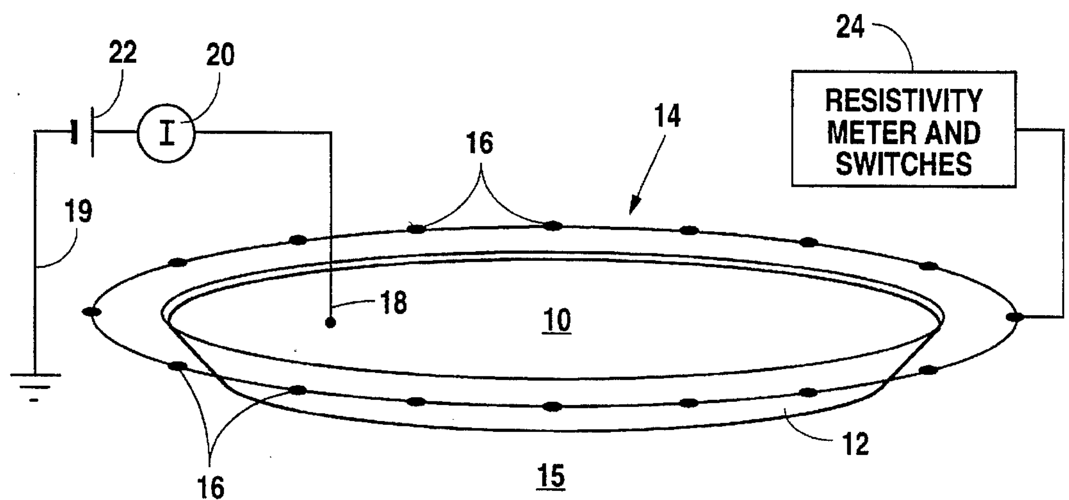
FIG. 1 is a schematic perspective view of a sensor system appropriate for implementation of the method of the present invention.

A system appropriate for implementation of the methods of the present invention is shown schematically in FIG. 1. A series of electrodes (16), placed at intervals, are used to make the necessary voltage and resistivity measurements. While the position of these electrodes (16) must be known, they may be located inside or outside of facility (14) or both, or between two geomembrane liners (not shown) for double-lined facilities. The methods of the present invention can be used for non-insulated steel or concrete tanks as long as there is an identifiable electrical contrast between liquid (10) in containment facility (14) and the surrounding sub-grade (15).

Two electrodes (18) and (19) are used to inject a current into containment facility (14). One electrode, source electrode (18), is placed inside facility (14) within the bounds of liner (12) and the second electrode, sink electrode (19), is placed at a remote distance outside facility (14) in the surrounding soil (15). In an alternative embodiment for double-lined geomembrane facilities, sink electrode (19) may be placed in the leak detection zone (not shown) for locating leaks in the primary (upper) liner. For locating leaks in the secondary (lower) liner source electrode (18) is placed within the leak detection zone and sink electrode (19) is again placed outside of facility (14) at a remote location.

Source electrode (18), located within facility (14), may be charged by power source (22) and a resultant potential voltage may be measured between pairs of electrodes (16). As an alternative, a single remote potential measurement electrode (not shown) could be used as the second electrode in the pair to measure the resultant potential voltage.

When source (18) and sink (19) electrodes (drive electrodes) are electrically excited, electric current will flow within contents (10) of facility (14) to a leak point, through liner (12) at the leak point, and through subsurface soil (15) to return to sink electrode (19). If there is no leak, no current will flow in this circuit (for a facility isolated by an electrically insulating liner).

The current flow path will produce an electrical potential distribution within subsurface soil (15) outside facility (14) as well as inside stored material (10). One or both of these electrical potential distributions can be measured with sensing electrodes. Electrodes (16) in FIG. 1 are placed to measure only the potential outside the facility. The exact distribution of the electrical potential is dependent upon the location of drive electrodes (18) and (19), the strength of the drive potential (the current magnitude), the location of the leak, and the resistivity distribution of both stored material (10) and subsurface soil (15).

The location of drive electrodes (18) and (19) is assumed to be known. The current magnitude may be measured with ammeter (20). The resistivity distribution can be approximated (a uniform or constant value for example) or it may be calculated separately using Electrical Resistance Tomography (ERT) data gathered from electrodes (16) as described in more detail below. The potential distribution may be determined by measuring the potential difference between multiple combinations of sensing electrodes (16) also as described in more detail below.

The process of carrying out the methods of the present invention can best be described by again referring to FIG. 1. One electrode (18) is placed inside facility contents (10) and a second electrode (19) is placed in subsurface soil (15) outside facility (14). An electrical potential is created between electrodes (18) and (19) (for example, by battery (22)) and the current in this circuit is measured using ammeter (20). If the contents of facility (14) are electrically isolated from sub-soil (15) by geomembrane liner (12), no current, or a very small current, will be measured by ammeter (20) since geomembrane liner (12) is very resistive. If there is a leak in liner (12), a current will flow between electrodes (18) and (19), through facility contents (10), through the leak, and through sub-soil (15). The presence of this current will denote an electrical leak through liner (12) as long as facility contents (10) are in all other ways electrically isolated from sub-soil (15). That is, there are no conducting pipes, drains, etc., and no fluid or damp dirt between contents (10) and sub-soil (15).

1. Electrical Potential Distribution—Method 1

In a first preferred method of the present invention, the leak is located by using the fact that an electrical current between electrodes (18) and (19) will produce an electric potential distribution within sub-soil (15) outside facility (14) and within contents (10) of the facility. Measurement of this potential distribution in either or both places can be used to locate the position of the leak. For simplicity, the description of how the leak is located will assume that there is only a single leak, although the methods associated with the present invention will work just as well when there is more than one leak.

Electrodes (16) are placed in soil (15) just outside and around the periphery of geomembrane liner (12). Electrodes (16) are used to sample the electric potential. A number of measurements of the potential can be made using various combinations of electrode pairs. Alternatively, potentials can be measured between each of electrodes (16) and a single electrode (not shown) at some distance (far afield) from facility (14). In either case, these measurements sample the potential distribution established by the electric current leak in the liner and current flow through the soil (15).

As indicated above, the measured potential distribution at electrodes (16) is a function of four variables: 1) the location of the leak (which will approximate an electric pole when current is flowing through it), 2) the location of electrode (19) (also an electric pole), 3) the magnitude of the current flowing between the leak and electrode (19) (as measured on ammeter (20)), and finally, 4) the electrical resistivity distribution in soil (15).

The location of the leak can be calculated if items 2–4 above are known. The location of electrode (19) is known. The current as measured by ammeter (20) is known. The unknown but determinable factor in this case is the electrical resistivity distribution in soil (15), which may either be assumed or calculated using other means described in more detail below.

In the first method of the present invention, either approach can be used. Assuming the character of the resistivity distribution will result in a calculated leak position that is in error. The magnitude of this error is determined by the accuracy of the assumption for the electrical resistivity distribution in the soil. That is, the error will be small if the soil is nearly uniform in electrical resistivity. However, it is not necessary to assume a resistivity distribution because electrodes (16) can be used to calculate such a distribution using electrical tomographic methods as described in Daily, W., Ramirez, A., LaBrecque, D., Barber, W., Electrical Resistance Tomography Experiments at the Oregon Graduate Institute, *Journal of Applied Geophysics*, No. 33, (1995), which descriptions are incorporated herein by reference.

In either case, once the resistivity distribution of the sub-surface material is assumed or calculated, the leak location can be calculated using several approaches. As a first example, a potential is calculated at each electrode position (16) for an electric pole (leak) of some arbitrary magnitude and position. This calculation can be analytical for simple cases or numerical for more complex geometries. The location and magnitude of this pole are adjusted to reduce the size of the squared difference between the measured potential and the calculated potential at each electrode (16). Using this new source pole representing the leak, the potentials are recalculated at each electrode (16). Adjusting the pole location again to reduce the squared difference between the measured and calculated potentials brings the location closer to the actual leak. This iterative process is continued until the squared difference has been reduced to some predetermined small value. At this point, the calculated leak location may be assumed to be a good approximation of the actual location.

In a second calculation example, an analytic or numerical model is constructed of several electric poles spread over the area of the geomembrane liner. Each pole has a known, fixed location but an unknown magnitude. The potential at each electrode (16) is calculated as a superposition of potentials of each pole. The resulting system of equations is solved for the magnitude of each pole which is consistent with the measured potential data. A large magnitude will be calculated for a pole which best represents (and is closest to) the leak in the liner, while other poles will have a small or zero magnitude.

This information gathered as described above is sufficient to calculate the location of the current flow through liner (12) forming facility boundary (14). As indicated, this calculation can be accomplished using a number of methods.

In summary, the first preferred method of the present invention is as follows:

1. Calculate the electrical potential distribution resulting from some arbitrary leak location and magnitude. Such a calculation can be simplified by assuming the leak is an electric pole at some location and of some specific strength and further assuming resistivity to be of some constant value or distribution.
2. Measure the potential distribution resulting from the actual leak.
3. Adjust the location and strength of the arbitrary source pole to reduce the magnitude of the squared difference between the measured potentials and the calculated potentials Daily, et al. *Journal of Applied Geophysics*, (1995).
4. Use this new source pole representing the leak and recalculate the potential.
5. Adjust this pole location to again reduce the squared difference between the measured and calculated potentials.
6. Continue the iterative process until the squared difference has been reduced to some predetermined small value. At this point, the calculated leak location is assumed to be a good approximation of the actual location.

Figure 5:
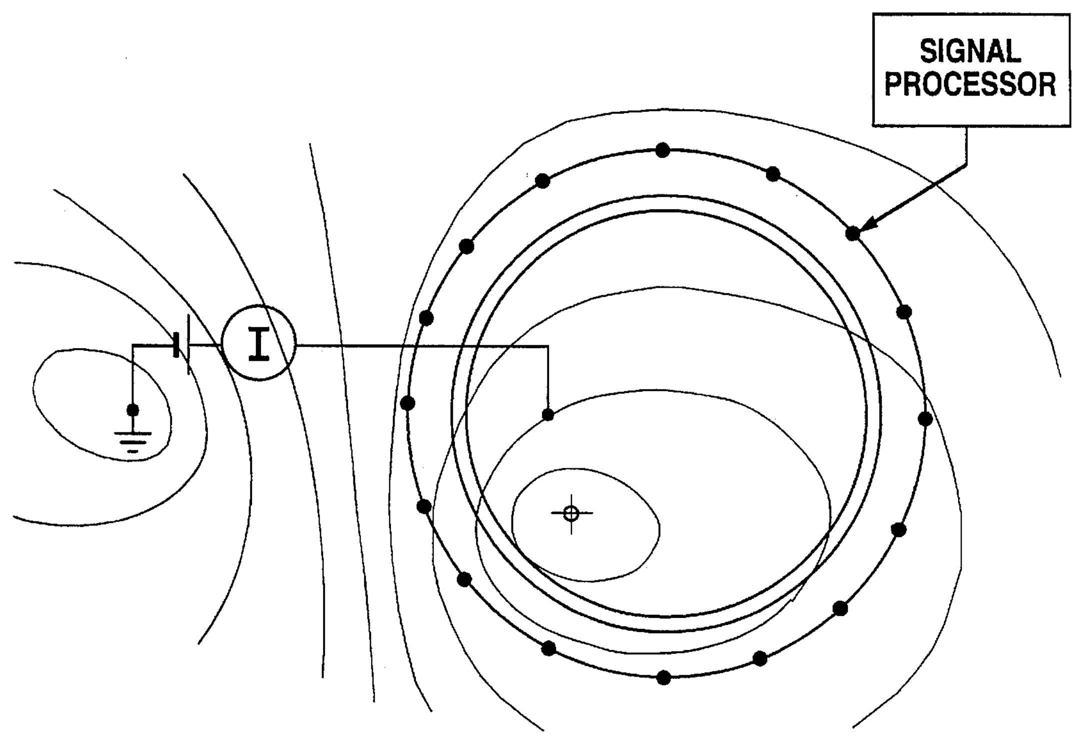
FIG. 5 is a graphic plan view of equipotential lines resulting from the Use of a source electrode within the containment and a sink electrode remote from the containment and the passage of a current through an actual leak in the facility.

FIG. 5 relates to the first preferred method of the present invention wherein a source and sink electrode drive an electric potential between the material contained within the facility and a remote sink electrode outside the facility. This driving voltage creates an electrical potential distribution that centers on the sink electrode and on the leak location acting as a source pole. Again the array of electrodes surrounding the containment facility measure the potential at various locations in a manner that permits accurate characterization of the potential distribution.

Figure 6:
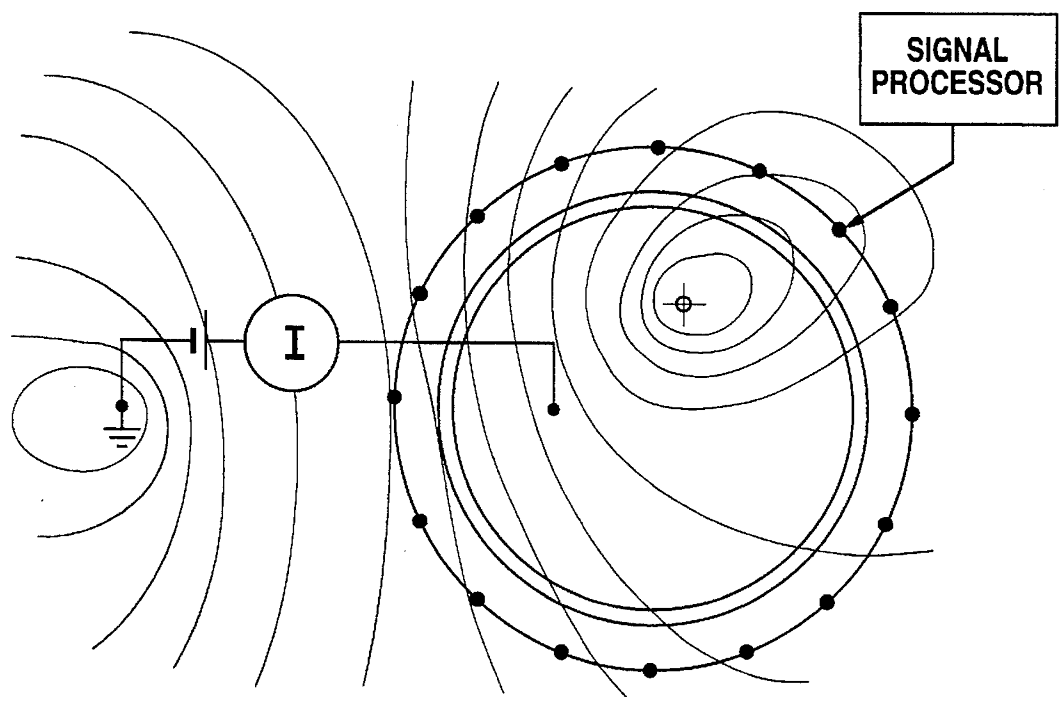
FIG. 6 is a graphic plan view of equipotential lines resulting from the use of a source electrode within the containment and a sink electrode remote from the containment and the passage of a current through an arbitrary point in the facility, predicting the effects of an actual leak.

FIG. 6 discloses an example of a first arbitrary source pole (leak location) utilized to predict the electrical potential distribution and to create a set of data that is compared to the measured distribution shown in FIG. 5. This arbitrary electrical potential distribution is modified by modifying the location of the theoretical leak, whereby the resultant is again compared with the actual measurements. By the iterative process described above, the arbitrary location of FIG. 6 will become closer to the actual location described in FIG. 5.

2. Electrical Resistivity Tomography—Method 2

The above described first preferred method of the present invention involves a process of predicting and measuring electric potential distribution resulting from a current flow brought about by a leak in the containment facility. This first preferred method depends to some extent on an assumption regarding the electrical resistivity of the sub-surface soil surrounding the containment facility. In most cases, valid assumptions can be made regarding the electrical resistivity distribution that still provides a basis for accurately approximating the location of the leak. The present invention, however, includes methodology designed to either 1) provide a more accurate profile of the electrical resistivity distribution within the sub-surface soil for the purpose of carrying out the first preferred method, or 2) establishing a base-line resistivity profile that can be compared to modified resistivity profiles that result when a leak of conductive fluid does occur. In either case, the relatively simple and straightforward array of sensors similar to those described above with respect to FIG. 1, can be utilized to accomplish a mapping of the resistivity profile without the need for complex grid of sensors.

The process of calculating the actual electrical resistivity distribution can best be described by reference to FIG. 3.

Specifically, the measurement process involves establishing a source and a sink electrode pair, source electrode (31)—sink electrode (33), for example, and measuring an electrical potential at each of the other electrodes (39)–(46) positioned about facility (14). The result is a large array of electrical potential values organized in sets associated with a specific source and sink electrode pair. In other words, starting with each individual electrode in the array, two variations create a number of combinations and data values. Starting with electrode (31), for example, as a source electrode, each of the remaining electrodes (32)–(46) may be utilized as a sink electrode. For each of these source dipole combinations, potential measurements are made at each dipole which can be formed of the remaining fourteen electrodes not utilized in the voltage pair.

Figure 2:
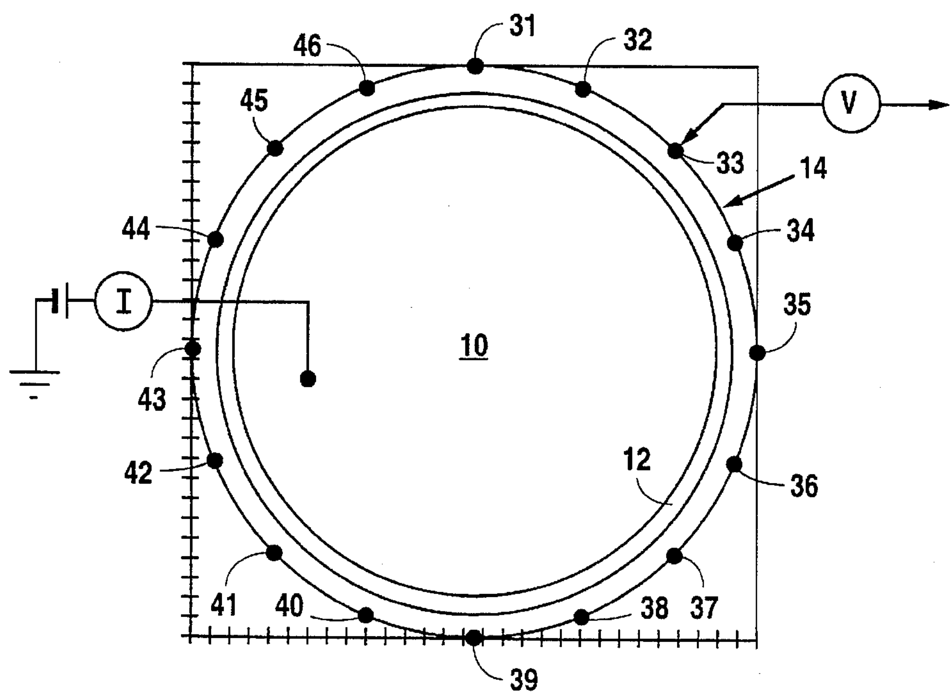
FIG. 2 is a plan view of the sensor system shown in FIG. 1, incorporating graphic coordinate axes to show the implementation of the method of the present invention.

Thus, for a particular electrode pair utilized as a source dipole, there would be 14×13 or 182 individual electrical potential measurements that are made. Multiply this by a total of 16×15 or 140 source dipole possibilities, shown as an example in FIG. 2, and a total of 43,680 values are available to characterize the electrical resistivity of the soil material beneath the surface of the containment facility. (Not all of these data values are independent and in practice only a subset of these data values would be used.) Well known tomographic imaging techniques are utilized to convert this data array to establish a two-dimensional or three-dimensional array of resistivity values for the soil.

Figure 4:
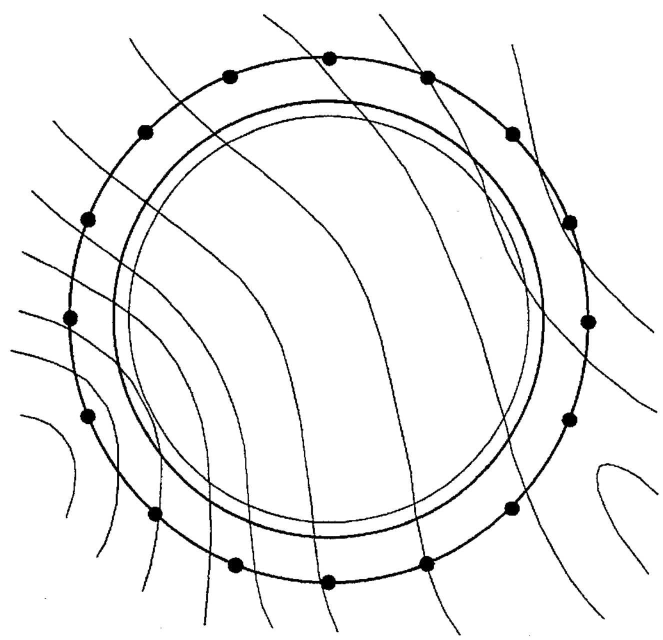
FIG. 4 is a graphic plan view of lines of equal resistivity resulting from the application of Electrical Resistivity Tomography (ERT) techniques to potential data similar to that derived in FIG. 3.

Although in reality the containment facility is a three-dimensional volume, for the purposes of leak location the depth of such facilities is usually small compared with its surface dimensions. The tomographic resistivity data, therefore, may often be treated as two-dimensional and may be visualized in the plan view as shown in FIG. 4.

In the most well explored fields of computer tomography (CT) reconstruction, the probing energy is typically high-energy x-rays with straight ray paths that are independent of the medium being probed. In contrast, the current paths (and equipotential lines) of ERT in the present case are functions of the unknown resistivity distribution. This leads to a non-linear reconstruction problem in which questions of algorithmic convergence must be addressed. Various reconstruction algorithms based upon an iterative linearization of the non-linear relationship between the resistivity distribution and the electrical measurements are known and applicable. Several interactive computer programs are available for making these calculations that incorporate reconstruction algorithms such as found in LaBrecque (1989) and Daily et al. (1995).

In this second preferred method of the present invention a base-line electrical resistivity profile, is compared with subsequent resistivity profiles. Assuming once again that the material contained within a lined containment facility includes liquids and the like, it is apparent that leakage of such liquids may result in a change in the electrical resistivity distribution in the soil beneath the containment facility. The electrical resistivity tomography methods described above, therefore, can be used to provide a base-line resistivity distribution against which future resistivity distributions may be compared. Specifically, a sub-surface area with a known electrical resistivity distribution will experience decreased resistivity in the sub-surface soil in the area immediately adjacent the leak of conductive liquid. The process involves repeating the measurements made initially for a containment facility known to have no leaks, with subsequent measurements made over time. As long as extraneous factors can be eliminated as affecting changes in the resistivity distribution, any such deviations from the base-line distribution can be identified as having derived from leakage through the liner. The specific characteristics of the changes in the distribution will identify not only the location but also the magnitude of the leak if it occurs.

Figure 3:
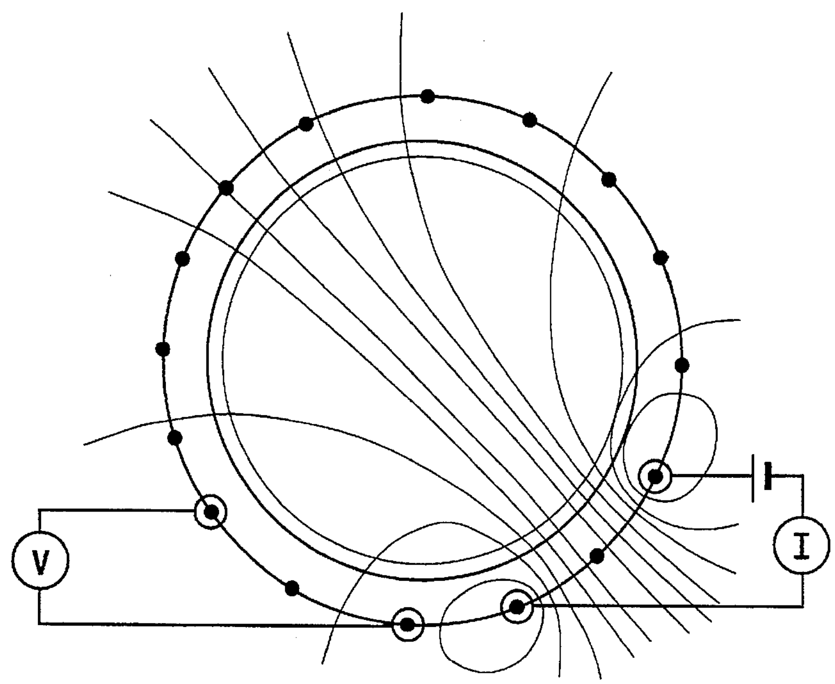
FIG. 3 is a graphic plan view of equipotential lines resulting from the use of two peripheral array electrodes as a source and sink voltage pair.

FIG. 3 discloses an example of an electric dipole produced between two electrodes in an array of the type shown generally in FIG. 1. The electric dipole creates an electrical potential distribution that is measurable at each of the remaining electrodes in the array. Moving the electric dipole from one electrode pair to another and, thereafter, making electrical potential measurements at each of the remaining electrodes provides the amount of data necessary to characterize the electrical resistivity profile for the sub-surface soil under the containment facility.

FIG. 4 discloses the resultant electrical resistivity distribution that might be determined from the series of potential measurements made as described in FIG. 3. Lines of equal resistivity may result from specific geologic structures in the sub-surface soil or from previous contamination the soil by conductive liquids. It should be noted that gradual, non-localized changes in the resistivity profile of the sub-surface soil might be expected and can be tracked and distinguished from more dramatic localized changes in the profile brought on by the occurrence of leaks within the facility.

The methods of the present invention described above that utilize both characterizations of electrical potential distribution and characterizations of electrical resistivity distribution, have been described specifically in conjunction with facilities that use geomembrane, non-conductive containers. As indicated earlier, however, these methods can be utilized in conjunction with electrically conducting containers such as steel and concrete tanks, wherein each electrical potential data collected from the sensing electrodes is formed from the comparison of two potential measurements. The first of these two potential measurements is taken before the leak occurs and the second taken after the leak has occurred. For Method 1, current flows from electrode (18), through the facility contents, as well as through the containment vessel or liner at many paths, not just the path of the leak, and then through the soil outside the facility to sink electrode (19).

When a leak does occur, the conductive fluid leaves the facility and moves into the sub-soil beneath the barrier making that soil more conductive. This increase in electrical conductivity of the soil causes more electric current to flow from the barrier at this location. After the leak, the potential measured on the electrical potential sensing electrodes (16) is a superposition of potentials from the current flowing before the leak and that flowing after with the extra current flowing after the leak through this region of enhanced electrical conductivity. Therefore, subtracting the potential measured before the leak from that measured after the leak leaves the potential which would be measured if only the extra current were flowing from the barrier at the leak point. This reduces the case to that described above with an electrically insulating geomembrane-type liner and the location of the current source can be found according to the methods identified.

Likewise for Method 2, changes in electrical resistivity distribution can be identified even where the containment facility is maintained with an electrically conductive liner. Because it is the change in the resistivity distribution that determines the existence and location of a leak, the presence or absence of an electrically conductive liner is not essential to the determination. As long as the liquid contained within the facility is itself electrically conductive and redistributes the resistivity profile when leaking from the facility, both the method involving electrical potential distribution (Method 1) and the method involving electrical resistivity distribution (Method 2), as well as the combination of the two described above, will be effective for isolating the location and magnitude of a leak.

Although this invention has been described with reference to specific embodiments, this description is not meant to be construed in a limiting sense. Various modifications of the disclosed embodiment, as well as alternative embodiments of the invention, will become apparent to persons skilled in the art upon reference to the description of the invention. It is therefore contemplated that the appended claims will cover such modifications that fall within the true scope of the invention.

We claim:

1. A method for detecting and locating leaks in a geomembrane lined facility containing liquids, sludges, or soils, using an excitation of the mass (mise-á-la-masse) electrical resistivity technique and an electrode array, comprising the steps of:

placing a plurality of electrical potential sensing electrodes in soil located peripherally outside said lined facility;

making a first set of electrical potential measurements on combinations of said sensing electrodes using a first sensing electrode pair as a current injection pair and a second sensing electrode pair as an electrical potential measurement pair;

mapping an electrical resistivity distribution under said lined facility, said distribution derived from said first set of electrical potential measurements by performing a mathematical inversion on said first set of electrical potential measurements;

injecting an electrical current into said liquid; sludge, or solid using an injection electrode located within said lined facility and a sink electrode located in an area outside of said lined facility;

making a second set of electrical potential measurements on combinations or said sensing electrodes located peripherally outside said lined facility; and analyzing said second set of electrical potential measurements using mathematical inversion techniques to locate said leaks in said lined facility.

2. A method for detecting and locating leaks in a geomembrane-lined facility or an electrically conducting facility containing liquids, sludges, or soils, using electrical resistivity tomography (ERT) techniques and an electrode array comprising the steps of:

placing a plurality of electrical resistance sensing electrodes in soil located peripherally outside said lined facility;

making a first set of electrical resistance measurements on combinations of said sensing electrodes;

mapping a no-leak electrical resistivity distribution by performing a mathematical inversion on said first set of electrical resistance measurements made under said lined facility;

mapping a second electrical resistivity distribution by performing a mathematical inversion on electrical resistance measurements under said lined facility at a point later in time than said first set of measurements; and comparing said no-leak electrical resistivity distribution with said second electrical resistivity distribution and identifying differences of conductivity in said soil located beneath or peripherally about said lined facility, said differences in conductivity being indicative of a location of said leak.

3. A method for detecting and locating leaks in electrically conducting containers containing liquids, sludges, or soils, using an excitation of the mass electrical resistivity technique and an electrode array comprising the steps of:

placing a plurality of electrical potential sensing electrodes in soil located peripherally outside said container;

injecting an electrical current into said liquid, sludge, or soil using an injection electrode located within said container and a sink electrode located in an area outside of said container;

making a first set of electrical potential measurements before a leak develops using said peripheral sensing electrodes;

making a second set of electrical potential measurements after said leak develops using said peripheral sensing electrodes;

subtracting said first set of electrical potential measurements from said second set of electrical potential measurements; and analyzing said subtracted set of electrical potential measurements using mathematical inversion techniques to locate said leaks in said container.

* * * * *